US012624360B2

(12) United States Patent
Coates

(10) Patent No.: US 12,624,360 B2
(45) Date of Patent: May 12, 2026

(54) MICROBIAL RESPIRATION OF CHLOROXYANIONS AS A SOURCE OF OXYGEN FOR BIOPROCESSING

(71) Applicant: The Regents of the University of California, Oakland, CA (US)

(72) Inventor: John D. Coates, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 388 days.

(21) Appl. No.: 18/313,367

(22) Filed: May 7, 2023

(65) Prior Publication Data

US 2023/0272404 A1 Aug. 31, 2023

Related U.S. Application Data

(63) Continuation of application No. PCT/US2022/011004, filed on Jan. 3, 2022.

(60) Provisional application No. 63/134,179, filed on Jan. 5, 2021.

(51) Int. Cl.
| | |
|---|---|
| *C12N 15/52* | (2006.01) |
| *C12N 1/21* | (2006.01) |
| *C12N 9/02* | (2006.01) |
| *C12P 7/625* | (2022.01) |

(52) U.S. Cl.
CPC ........... *C12N 15/52* (2013.01); *C12N 9/0004* (2013.01); *C12N 9/0069* (2013.01); *C12P 7/625* (2013.01); *C12Y 107/02001* (2013.01); *C12Y 108/05003* (2013.01); *C12Y 113/11049* (2013.01); *C12Y 197/01001* (2013.01)

(58) Field of Classification Search
None
See application file for complete search history.

(56) References Cited

U.S. PATENT DOCUMENTS

| | | |
|---|---|---|
| 2016/0068875 A1 | 3/2016 | Criddle et al. |
| 2017/0283685 A1 | 10/2017 | Coates |
| 2019/0119706 A1* | 4/2019 | Tappel .................... C12P 7/625 |

FOREIGN PATENT DOCUMENTS

WO 2013070949 5/2013

OTHER PUBLICATIONS

Sutton, Bioreactor Configurations for Ex-Situ Treatment of Perchlorate: A Review, Water environment research 78.13, 2006, 2417-2427. (Year: 2006).*

Carlstrom et al., Linking methane oxidation with perchlorate reduction: a microbial base for possible Martian life, American Geophysical Union, Fall Meeting 2011, abstract id B51G-0485. (Year: 2011).*

Extended European Search Report for related EP 22736971.7, 9 pages (Aug. 21, 2024).

Clark I. C. et al: "Synthetic and Evolutionary Construction of a Chlorate-Reducing Shewanella oneidensis MR-1", MBIO, vol. 6, No. 3, May 19, 2015 (May 19, 2015), pp. 1-10, XP093193560, US.

Carlstrom C I. et al: "Physiological and Genetic Description of Dissimilatory Perchlorate Reduction by the Novel Marine Bacterium *Acrobacter* sp. Strain CAB", MBIO, vol. 4, No. 3, May 21, 2013 (May 21, 2013), pp. 1-9, XP093193910, US.

Barnum T. P. et al: "An uncharacterized clade in the DMSO reductase family of molybdenum oxidoreductases is a new type of chlorate reductase", Environmental Microbiology Reports, Wiley-Blackwell Publishing, GB, vol. 12, No. 5, Aug. 10, 2020 (Aug. 10, 2020), pp. 534-539, XP072399757.

International Search Report for priority PCT/US2022/011004, 11 pages (Mar. 24, 2022).

* cited by examiner

*Primary Examiner* — Todd M Epstein
(74) *Attorney, Agent, or Firm* — Richard Aron Osman

(57) ABSTRACT

Aerobic microbial processes comprise culturing microbes comprising a (per)chlorate respiration pathway in a bioreactor in a bioprocess employing microbial respiration of chloroxyanions as a source of oxygen for the bioprocess, in the absence of external addition of molecular oxygen.

1 Claim, 1 Drawing Sheet

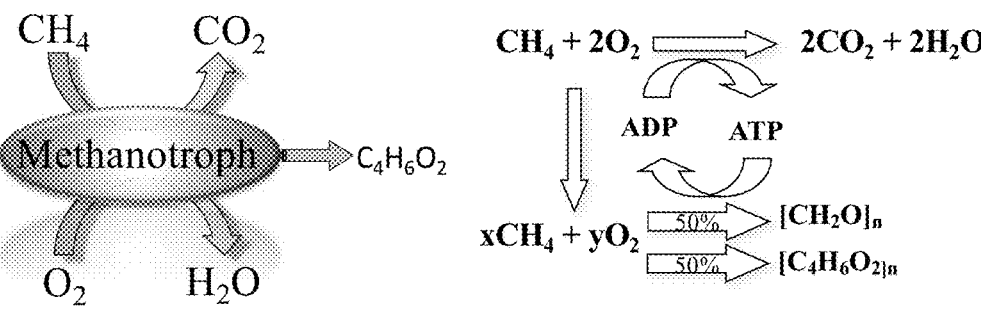
Fig. 1A                               Fig. 1B
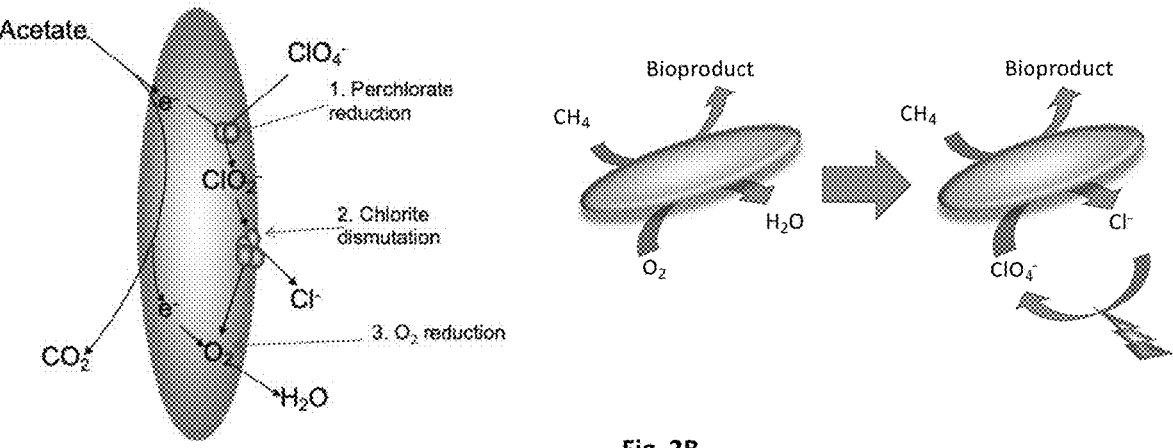
Fig. 2A                           Fig. 2B
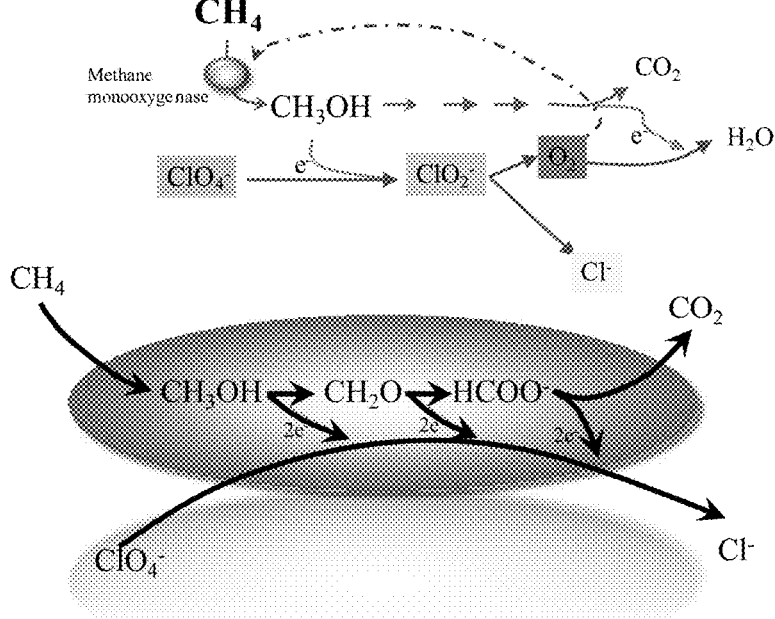
Fig. 2C

MICROBIAL RESPIRATION OF CHLOROXYANIONS AS A SOURCE OF OXYGEN FOR BIOPROCESSING

The bioeconomy has estimated an annual value of $960B or 5% of the 2016 US GDP. The bioeconomy was also recently recognized in a US National Academy of Science report as a burgeoning field of opportunity, both to ameliorate climate change and to move away from petrochemicals towards a sustainable future. While the bioeconomy is based on any process that involves the sustainable conversion of biological material into products, i.e. bio-based chemicals, fuels, plastics, building materials, etc., biotechnology is the purported primary mode manufacturing. The majority of industrial microbial processes are based on aerobic metabolisms because of the favorable biochemical energetics and metabolic versatility of aerobic microorganisms. However, these processes are conversely the most energy intensive due to the extensive agitation required to dissolve poorly soluble oxygen into an aqueous system. While anaerobic microbial processes are preferential due to the significant cost savings, many microbial transformations require molecular oxygen as a co-substrate. These costs can be as much as 50% of the capex and 20% of operational costs. Furthermore, the energy required is often sourced from fossil fuels significantly offsetting the environmental benefits of the sustainable process. Quite often, it is the burden of these costs that prevent biotechnological processes from competing successfully with existing petrochemical manufacturing, especially for commodity chemicals. For example, while there are several organisms known that can produce bioplastics from sustainable feedstocks, these are prevented from successfully penetrating the market because of the additional cost premium when compared to petrochemical plastics.

We previously disclosed Synthetic and Evolutionary Construction of a Chlorate-Reducing *Shewanella oneidensis* MR-1, Iain C. Clark, et al.,2015, mBio 6(3) e00282-15: and (Per)Chlorate-Reducing Bacteria Can Utilize Aerobic and Anaerobic Pathways of Aromatic Degradation with (Per) Chlorate as an Electron Acceptor, Charlotte I. Carlström, et al., 2015, mBio 6 (3) e02287-14. These basic research projects provided further biochemical and genetic insight into the respiratory (per)chlorate reduction pathway and identification of components. The present invention takes advantage of these findings, as well as our research showing that (per)chlorate can be metabolized to provide oxygen under anaerobic conditions to allow for oxygen dependent metabolisms, to provide novel bioreactors and bioprocesses. The invention overcomes prior limitations and allows for aerobic microbial processes in the absence of the external addition of molecular oxygen or the need for energy-intensive agitation required for oxygen dissolution.

SUMMARY OF THE INVENTION

The invention provides novel bioreactors and bioprocesses employing microbial respiration of chloroxyanions as a source of oxygen for industrial-scale bioprocessing productions.

In an aspect, the invention provides a method of aerobic microbial processing comprising: culturing microbes comprising a (per)chlorate respiration pathway in a bioreactor in a bioprocess employing microbial respiration of chloroxyanions as a source of oxygen for the bioprocess, in the absence of external addition of molecular oxygen.

In embodiments:

the bioprocess comprises production of drugs, commercial or industrial enzymes, bioplastics or bioplastic precursors, biofuels or biofuel precursors, commodity chemicals, cosmetics, foods, such as plant-protein based meat substitutes, or food additives, such as citric acid;

the microbes are obligately aerobic methanotrophic, and the bioprocessing converts the greenhouse gas methane ($CH_4$) into the biopolymer polyhydroxybutyrate (PHB), polyhydroxyalkanoate (PHA), or polylactic acid (PLA);

the microbes are obligately aerobic eukaryotic fungi, and the bioprocess utilizes complex lignin-celluosic feedstocks;

the microbial respiration comprises a pathway comprising: (i) reduction of (per)chlorate to chlorite ($ClO_2^-$) by perchlorate reductase; (ii) dismutation of chlorite into chloride and molecular oxygen ($O_2$) by chlorite dismutase; and (iii) reduction of molecular oxygen by cytochrome oxidase;

the microbial respiration comprises a pathway comprising: (i) reduction of chlorate to chlorite ($ClO_2^-$) by a protein belonging to the DMSO reductase superfamily of molybdopterin oxidoreductases; (ii) dismutation of chlorite into chloride and molecular oxygen ($O_2$) by chlorite dismutase; and (iii) reduction of molecular oxygen by cytochrome oxidase;

the microbial (per)chlorate respiration pathway is engineered;

the microbes are genetically engineered to comprise an operative microbial (per)chlorate respiration pathway encoding: (i) a perchlorate reductase which effects reduction of (per)chlorate to chlorite ($ClO_2^-$); (ii) a chlorite dismutase which effects dismutation of the chlorite into chloride and molecular oxygen ($O_2$); and (iii) a cytochrome oxidase which effects reduction of the molecular oxygen; wherein the pathway enables the engineered microbe to grow in the bioreactor with (per)chlorate as its sole electron acceptor in the absence of oxygen; and/or the microbes are genetically engineered to comprise an operative microbial (per)chlorate respiration pathway encoding: (i) a protein belonging to the DMSO reductase superfamily of molybdopterin oxidoreductases which effects reduction of (per)chlorate to chlorite ($ClO_2^-$); (ii) a chlorite dismutase which effects dismutation of the chlorite into chloride and molecular oxygen ($O_2$); and (iii) a cytochrome oxidase which effects reduction of the molecular oxygen; wherein the pathway enables the engineered microbe to grow in the bioreactor with (per)chlorate as its sole electron acceptor in the absence of oxygen.

In an aspect, the invention provides a bioreactor configured for a method aerobic microbial processing comprising: culturing microbes comprising a (per)chlorate respiration pathway in a bioreactor in a bioprocess employing microbial respiration of chloroxyanions as a source of oxygen for the bioprocess, in the absence of external addition of molecular oxygen. the bioreactor with (per)chlorate as its sole electron acceptor in the absence of oxygen.

In embodiments:

the bioprocess comprises production of drugs, commercial or industrial enzymes, bioplastics, biofuels or biofuel precursors, commodity chemicals, cosmetics, foods, such as plant-protein based meat substitutes, or food additives, such as citric acid;

the microbes are obligately aerobic methanotrophic, and the bioprocessing converts the greenhouse gas methane ($CH_4$) into the biopolymer polyhydroxybutyrate (PHB);

polyhydroxyalkanoate (PHA) or polylactic acid (PLA)

the microbes are obligately aerobic eukaryotic fungi, and the bioprocess utilizes complex lignin-celluosic feedstocks;

the microbial respiration comprises a pathway comprising: (i) reduction of (per)chlorate to chlorite ($ClO_2^-$) by perchlorate reductase; (ii) dismutation of chlorite into chloride and molecular oxygen ($O_2$) by chlorite dismutase; and (iii) reduction of molecular oxygen by cytochrome oxidase;

the microbial respiration comprises a pathway comprising: (i) reduction of chlorate to chlorite ($ClO_2^-$) by a protein belonging to the DMSO reductase superfamily of molybdopterin oxidoreductases; (ii) dismutation of chlorite into chloride and molecular oxygen ($O_2$) by chlorite dismutase; and (iii) reduction of molecular oxygen by cytochrome oxidase;

the microbial (per)chlorate respiration pathway is engineered;

the microbes are genetically engineered to comprise an operative microbial (per)chlorate respiration pathway encoding: (i) a perchlorate reductase which effects reduction of (per)chlorate to chlorite ($ClO_2^-$); (ii) a chlorite dismutase which effects dismutation of the chlorite into chloride and molecular oxygen ($O_2$); and (iii) a cytochrome oxidase which effects reduction of the molecular oxygen; wherein the pathway enables the engineered microbe to grow in the bioreactor with (per)chlorate as its sole electron acceptor in the absence of oxygen; and/or the microbes are genetically engineered to comprise an operative microbial (per)chlorate respiration pathway encoding: (i) a protein belonging to the DMSO reductase superfamily of molybdopterin oxidoreductases which effects reduction of (per)chlorate to chlorite ($ClO_2^-$); (ii) a chlorite dismutase which effects dismutation of the chlorite into chloride and molecular oxygen ($O_2$); and (iii) a cytochrome oxidase which effects reduction of the molecular oxygen; wherein the pathway enables the engineered microbe to grow in the bioreactor with (per)chlorate as its sole electron acceptor in the absence of oxygen.

The invention encompasses all combinations of the particular embodiments recited herein, as if each combination had been laboriously recited.

BRIEF DESCRIPTION OF THE DRAWINGS

FIG. 1A. Polyhydroxybutyrate (PHB): overview

FIG. 1B. PHB ($C_4H_6O_2$)n from methane: reactions

FIG. 2A. Perchlorate reduction: three-step process

FIG. 2B. Engineered anaerobic methane metabolism coupled to perchlorate

FIG. 2C. Direct $O_2$-dependent oxidation with $ClO_4^-$

DESCRIPTION OF PARTICULAR EMBODIMENTS OF THE INVENTION

Unless contraindicated or noted otherwise, in these descriptions and throughout this specification, the terms "a" and "an" mean one or more, the term "or" means and/or. It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein, including citations therein, are hereby incorporated by reference in their entirety for all purposes.

This invention takes advantage of the unique oxygen biogenesis biochemical pathway associated respiration of the chloroxyanions chlorate ($ClO_3^-$) and perchlorate ($ClO_4^-$) [collectively denoted (per)chlorate]. The invention provides for aerobic microbial processes in the absence of external addition of molecular oxygen. Canonical microbial (per)chlorate respiration is an energetically favorable process that involves three steps: (i) the reduction of (per) chlorate to chlorite ($ClO_2^-$) by the perchlorate reductase; (ii) disputation of chlorite into chloride and molecular oxygen ($O_2$) by the chlorite dismutase; and (iii) reduction of molecular oxygen by the cytochrome oxidase. In this way (per) chlorate respiring organisms can enzymatically produce oxygen under anoxic conditions. This provides organisms endowed with this pathway with a unique metabolic versatility, allowing them to use (per)chlorate not only as an electron acceptor but also as a co-substrate in oxygenase driven reactions in the absence of externally added oxygen. This pathway is well characterized with known biochemistry and genes. We have previously engineered this pathway into *Shewanella* species allowing the engineered strain to grow with chlorate as its sole electron acceptor in the absence of oxygen. An exemplary application of this invention is shown in FIGS. 1A-B and FIG. 2A-C, where the (per)chlorate pathway is engineered into an obligately aerobic methanotrophic organism to convert the greenhouse gas methane ($CH_4$) into the biopolymer polyhydroxybutyrate (PHB), a component of bioplastics. The bioplastics 2025 bioplastics predicted annual market value is $27.9 billion. Methanotrophs are intrinsically efficient at producing PHB and have been shown to accumulate as much as 67% of the cell biomass in the form of PHB. This often translates into titers of greater than 2 g $PHB.L^{-1}$ of culture which is sufficient for industrial production. In this process oxygen is used both as an electron acceptor and as a co-substrate for both cell growth and PHB production (FIGS. 1A-B and FIG. 2A-C). As such, these cultures often become oxygen limited requiring complex reactor designs and high energy inputs. Furthermore, these bioreactors are often operated at pressure of up to 3 atmospheres which represents an explosive hazard for mixed gasses of $CH_4$ and $O_2$. Perchlorate can overcome these limitations, as it is chemically stable, highly soluble (>67% by mass), and can be easily metabolized to provide both the energy and oxygen requirements of methanotrophy. Furthermore, perchlorate can be produced easily from renewable energy through electrochemical oxidation of sodium chloride (NaCl; table salt).

FIGS. 1A-1B: PHB production from methane is an oxygen intensive metabolism requiring 2 moles of $O_2$ per mole of $CH_4$ to grow the cells and 7 moles of $O_2$ per 8 moles of $CH_4$ to produce PHB.

67% dry wt biomass possible e.g. Wendlandt et al. (J Biotechnol. 2001 Mar. 30; 86(2):127-33) showed *Methylocystis trichosporium* sp. GB25 on methane at 3 atm yielded 4 g $L^{-1}H^{-1}$ biomass and 2 g $L^{-1}$ PHB with a yield of 0.55 g $g^{-1}$ $CH_4$. Glucose gives a yield of 0.3 to 0.4 gm PHB per gm glucose.

General Principle: $4n/x\ C_xH_yO_z \rightarrow (C_4H_6O_2)n + n[2y/x-3]$ $H_2O + n[1/2-(y-2z)/x]O_2$ $CH_4 => X=1;\ y=4;\ z=0$ $4n\ CH_4 + [n+n5/2]O_2 \rightarrow (C_4H_6O_2)n + n5\ H_2O$ For example, If n=2 then:

$$8 \; CH_4 + 7O_2 \rightarrow (C_4H_6O_2)_2 + 10 \; H_2O$$

Features: oxygen (energy) intensive process often leading to high risk (explosive) pressurized conditions in a bioreactor FIGS. 2A-2C: Perchlorate easily satisfies the oxygen requirement of methanotrophy and PHB production (or any other aerobic microbial process) through the unique biochemical pathway in which $ClO_4^-$ is converted into $O_2$ which then becomes available to the organism as an electron acceptor and co-substrate for by-product production. Features: •Perchlorate is well characterized •Perchlorate is highly soluble •Perchlorate is chemically stable •Perchlorate can be produced from renewable energy.

The invention claimed is:

1. A method of aerobic microbial processing comprising: culturing microbes comprising a (per)chlorate respiration pathway in a bioreactor in a bioprocess employing microbial respiration of chloroxyanions as a source of oxygen for the bioprocess, in the absence of external addition of molecular oxygen, wherein the microbes are genetically engineered to comprise an operative microbial (per)chlorate respiration pathway encoding:

(i) a perchlorate reductase which effects reduction of (per)chlorate to chlorite ($ClO_2^-$);

(ii) a chlorite dismutase which effects dismutation of the chlorite into chloride and molecular oxygen ($O_2$); and (iii) a cytochrome oxidase which effects reduction of the molecular oxygen;

wherein the pathway enables the engineered microbe to grow in the bioreactor with (per)chlorate as its sole electron acceptor in the absence of oxygen, wherein the microbes are obligately aerobic methanotrophs, that are Methylocystis trichosporium, and the bioprocess converts methane ($CH_4$) into polyhydroxybutyrate (PHB).

* * * * *